United States Patent [19]

McStravick et al.

[11] Patent Number: 4,817,633
[45] Date of Patent: Apr. 4, 1989

[54] LIGHTWEIGHT DEVICE TO STIMULATE AND MONITOR HUMAN VESTIBULO-OCULAR REFLEX

[75] Inventors: M. Catherine McStravick, Houston; David R. Proctor; Scott J. Wood, both of League City, all of Tex.

[73] Assignee: The United States of America as represented by the United States National Aeronautics and Space Administration, Washington, D.C.

[21] Appl. No.: 116,821

[22] Filed: Nov. 5, 1987

[51] Int. Cl.[4] .............................................. A61B 5/10
[52] U.S. Cl. ................................ 128/782; 2/6; 2/413; 2/421; 2/15; 2/425; 2/443; 128/202.11
[58] Field of Search ............... 128/745, 774, 777, 782, 128/201.29, 202.11; 2/6, 10, 15, 410-414, 417, 421-430, 443; 351/59, 155, 245

[56] References Cited

U.S. PATENT DOCUMENTS

| | | | |
|---|---|---|---|
| 2,847,003 | 8/1958 | Helmer et al. ........................ | 128/136 |
| 3,082,765 | 3/1963 | Helmer ................................ | 128/136 |
| 3,205,303 | 9/1965 | Bradley ................................ | 2/6 X |
| 3,548,411 | 12/1970 | Barston et al. ....................... | 2/6 |
| 3,748,657 | 7/1973 | Aileo .................................... | 2/6 |
| 3,783,452 | 1/1974 | Benson et al. ........................ | 2/6 |
| 4,023,209 | 5/1977 | Frieder, Jr. et al. ................. | 2/6 |
| 4,035,846 | 7/1977 | Jencks ................................. | 2/413 |
| 4,102,564 | 7/1978 | Michael .............................. | 351/245 X |
| 4,156,292 | 5/1979 | Helm et al. .......................... | 2/6 |
| 4,198,990 | 4/1980 | Higgins et al. ...................... | 128/782 |
| 4,259,747 | 4/1981 | Taesler et al. ....................... | 2/6 |
| 4,274,161 | 6/1981 | Littler ................................. | 2/413 |
| 4,405,213 | 9/1983 | Kolkmann ........................... | 351/59 |
| 4,581,774 | 4/1986 | Chaise ................................. | 2/421 |
| 4,586,200 | 5/1986 | Poon .................................... | 2/413 |
| 4,686,712 | 8/1987 | Spiva .................................. | 2/427 X |
| 4,703,879 | 11/1987 | Kastendieck et al. ............... | 2/6 X |

Primary Examiner—Kyle L. Howell
Assistant Examiner—Angela D. Sykes
Attorney, Agent, or Firm—Russell E. Schlorff; John R. Manning; Edward K. Fein

[57] ABSTRACT

A helmet formed of a rigid shell is disclosed. The shell is lined with several air filled bladders to contact firmly the head of a user. The shell has a rigid chin bar supporting a bite bar connected fixedly to a mouthpiece bearing against the teeth and hard palate to firmly anchor the helmet without movement. The outer shell surface supports various air pumping bulbs and accelerometers. Separate left and right visor pivot on the side guided in a central tongue and groove track to move optical lens mounts into the user's field of vision. The chin bar is connected to the shell by a pair of releasable clasps. A safety lanyard connects to the clasps to quickly pull pins from the clasps to enable quick release in case of motion sickness.

18 Claims, 3 Drawing Sheets

LIGHTWEIGHT DEVICE TO STIMULATE AND MONITOR HUMAN VESTIBULO-OCULAR REFLEX

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Technical Field of the Invention

The field of invention of this invention is a specialty helmet for supporting optical equipment in close proximity to the eyes of a subject for making specific eye stimulation and reflex measurements. It is extremely important that the optical equipment be fixed relative to the helmet and the helmet in turn fixed relative to the head of the subject. Slippage or movement between the subject's head and the helmet creates incorrect data and to this end, the present apparatus is a structure which can be coupled to the head of the subject (by rigid attachment to the skull without slippage) such that accurate data can be obtained. Moreover, it selectively mounts and dismounts as required appropriate optical equipment for making measurements of the subject.

2. Discussion of Background Art

References known to exist and having a bearing on the subject matter of the present disclosure include Jencks, U.S. Pat. No. 4,035,846. This shows an inflatable stabilization system located on the interior of an outside rigid helmet shell. There is an inflatable bladder having a number of fingers. The bladder is inflatable by operation of a manifold system connected to the bladder within the helmet.

Chaise U.S. Pat. No. 4,581,774 is a protective motorcycle helmet disclosing a collar and cooperative fastener below the collar. Helmer U.S. Pat. No. 3,082,765 shows a football helmet or the like having a chin strap with a cooperative mouthpiece adapted for protection of the mouth and teeth. Littler U.S. Pat. No. 4,274,161 shows a collar which has a tubular body enabling it to fit around a neck to conform beneath a crash helmet typically worn by a motorcycle driver. Poon U.S. Pat. No. 4,586,200 is a motorcycle driver helmet having a multiple skin construction in the helmet shell which enables air to be captured in bubbles within the structure. It conforms more readily to the fit, size and shape of the user's head.

Taesler U.S. Pat. No. 4,259,747 is a helmet for aircraft pilots. It has a mounting system for electronic communication devices. It includes cushions for supporting the head. Goggles are also supported on the helmet by means of appended arms.

BACKGROUND OF THE PRESENT DISCLOSURE

This disclosure is directed to a helmet which is particularly intended for use in measuring head and eye movement and also to enable the incorporation of an optical stimuli for neurosensory investigations. It requires significant design compromise to obtain such a helmet. The first criteria of the present invention is that it be fixed rigidly to the head. In large measure, helmets which are rigidly and snugly fixed to the head must fully enclose or envelope the head. Such helmets are available as for example for motorcycle drivers. They have secure latches and chin straps and fully encompass and enclose the head. However, such encompassing helmets are not acceptable for the kind of investigations which are necessary particularly in neurosensory investigations for astronauts. A large portion of the neurosensory investigation helmet must be cut away for electrodes, subject comfort, and also for extending visual field. In fact, so much of the helmet must be cut away that it is really not capable of fixedly attaching to the skull.

One of the important uses of the helmet of the present disclosure and one which necessitates a cut away helmet construction is investigation of human vestibulo-ocular reflex. This data relates to investigation and prevention of space adaptation syndrome. This refers generally to the fact that a significant portion of astronauts, that is personnel undergoing space travel in a near zero gravity field, experience in some fashion motion sickness. Typical motion sickness investigation primarily focuses on observations of the eyes of the personnel. One of the problems relating to an all encompassing helmet where the shell completely envelops the head is the possibility of space adaptation syndrome induced sickness which, in certain personnel, is manifested by nausea or vomiting. In view of that risk, it is necessary that the helmet dismount readily to free the person. Otherwise, there is a significant risk of choking, requiring the person to simultaneously attempt to pull off the helmet when they are gagging, thereby running the risk of choking to the person while simultaneously requiring complicated helmet removal activities.

One correction for such a helmet dismounting problem is to use a helmet which is substantially cut away. In other words, the total portion of helmet is reduced as, by example enlarging the face area, cutting back around the neck, and otherwise reducing the amount of shell. When this is done, the helmet typically becomes loose or slack on the head of the subject. Movement between the helmet and head of the subject during investigation creates false data. The present invention overcomes this handicap by providing a neurosensory investigation helmet with a plurality of inflatable bladders on the interior and a quick release chin bar connected to a mouthpiece securing the helmet in place. The bladders are placed on the interior so that they can be inflated pneumatically and thereby expand. The bladders enable the helmet to grip the head of the subject firmly. This assists in holding the helmet snugly on the head of the user. An important added factor is to fasten the helmet on the head of the user rigidly with respect to the skull. Clamping devices which engage the skull are terribly uncomfortable. However, it has been determined that the present apparatus can firmly grip and engage the skull by means of a mouthpiece constructed to fit around the upper teeth of the user and to bear against the hard palate just behind the front upper teeth. This is an area which is relatively insensitive, thereby permitting firm contact and engagement without discomfort to the user. Moreover, this type construction anchors the helmet so that it is not free to slide backwardly on the head of the user. This mouthpiece type construction in conjunction with inflatable bladders on the interior of the rigid shell permits the helmet of the present disclosure to be anchored firmly in place. That is, it is fixed but in a comfortable fashion to the head, even to the skull of the user. A release lanyard is provided to permit the user to quickly disengage the chin bar mouthpiece in the event of any distress.

The helmet of the present disclosure incorporates left and right visors which move independently of each other. They are adapted to pivot on the side of the helmet with a segment or wedge rotating in front of the eyes. There is a raised position where they are out of the way and there is a second position where they are immediately over the eye. The visors are constructed with a round opening. The opening is equipped with a lens mount such as the mounting ring commonly found for mounting lenses on a camera body. The size is such that a suitable optical system can be mounted to undertake experiments measuring space adaptation syndrome. This measurement particularly involves obtaining accurate, error free data from various devices which are fixed to the head by means of the helmet of the present disclosure. All relative movement is eliminated between the head, the helmet and the various sensors and measuring devices mounted on the helmet. This can be done in a comfortable, lightweight helmet enabling rather easy electrical and mechanical disconnection. Various stimulus modules and sensor modules are attached to the helmet at the visors. They can be connected on either visor, that is the visor over the left eye or the symmetrical visor over the right eye. The visors affix easily, rotate into and out of position and support interchangeable and detachable modules.

So that a full set of data can be obtained, ear phones are included inside the helmet so that communications can selectively be maintained with the subject. In the absence of communications, typically white noise is broadcast to the subject to mask off noise which might otherwise create noise triggered false data. There may also be variable tones (cadence) used to prompt the subject to make appropriate head movements. Likewise, the helmet is constructed with selected flat spots at proper locations for mounting accelerometer clusters at the indicated locations. The accelerometers are at right angles to one another in the cluster. This sensor indicates head movement so that it can be correlated with the optical measurements made at the eye, thereby assuring sufficient data for analysis of motion sickness.

The present apparatus is worn as a conventional helmet. It is placed on the head and then a chin bar is placed across the front. The chin bar supports an individualized mouthpiece which engages the front teeth and hard palate behind the teeth. To further couple the helmet and head, the helmet is provided with foam liners and air bladders. Integral air bladders are inflated to firmly yet gently grip the head of the user so that the entire system is fixed on the head with no possibility of movement between the head and helmet. Varied sized and interchangeable liners accommodate different head sizes. The various optical sensors and optical measuring devices are affixed to the visors so that the response of the subject can then be tested, observed and analyzed.

An important feature of the helmet of the present disclosure is that a lightweight device has been provided. At first blush, one might assume that the helmet is to be used in zero gravity circumstances and hence mass would therefore be meaningless. In actuality, mass is still meaningful because it is desirable to reduce inertia to the greatest extent possible. Accordingly, the disclosed helmet is reduced in weight by reducing the amount of shell around the head. Also, the accessories mounted on the helmet are also reduced. To this end, the helmet includes wiring and a plug for connection with a socket connecting to electrical conductors for remote location of most of the circuitry associated with the test accessories.

When the amount of helmet is reduced, lateral light leakage becomes more of a problem. In the event the helmet wraps completely around the head, outside light can be shut out. The cut away construction which is used in the present apparatus runs the risk of light leakage. Outside light is undesirable because it creates a false stimulus to the test subject. However, the use of the internal foam padding along the bridge of the nose and encircling the face along the cheekbones significantly cuts down the amount of leaked light. When the subject is undergoing experimentation, the risk of distraction from leaked light is then reduced.

In summary, the present apparatus is a cut away helmet with a reduced mass which nevertheless snugly and fixedly attaches to the head with comfort. It is attached in such a way that it is rigidly coupled to the skull. It is fixed by means of inflatable bladders and foam lining snugly gripping the back and sides of the head. The helmet cannot slide on the head by virtue of a chin bar supported customized mouthpiece bearing against the teeth and hard palate to fix the helmet firmly in place. The chin bar and mouthpiece are easily dismounted by a quick release lanyard pulling latch pins from the connectors on the helmet. The helmet includes left and right symmetrical visors which pivot on the sides of the helmet, the visors supporting circular eye openings which can selectively receive lenses for viewing or mount optical equipment for undergoing tests. An inflation system is included for the various bladders to assure clamping when the helmet is put on. The helmet also supports pairs of accelerometers to measure orientation in space.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
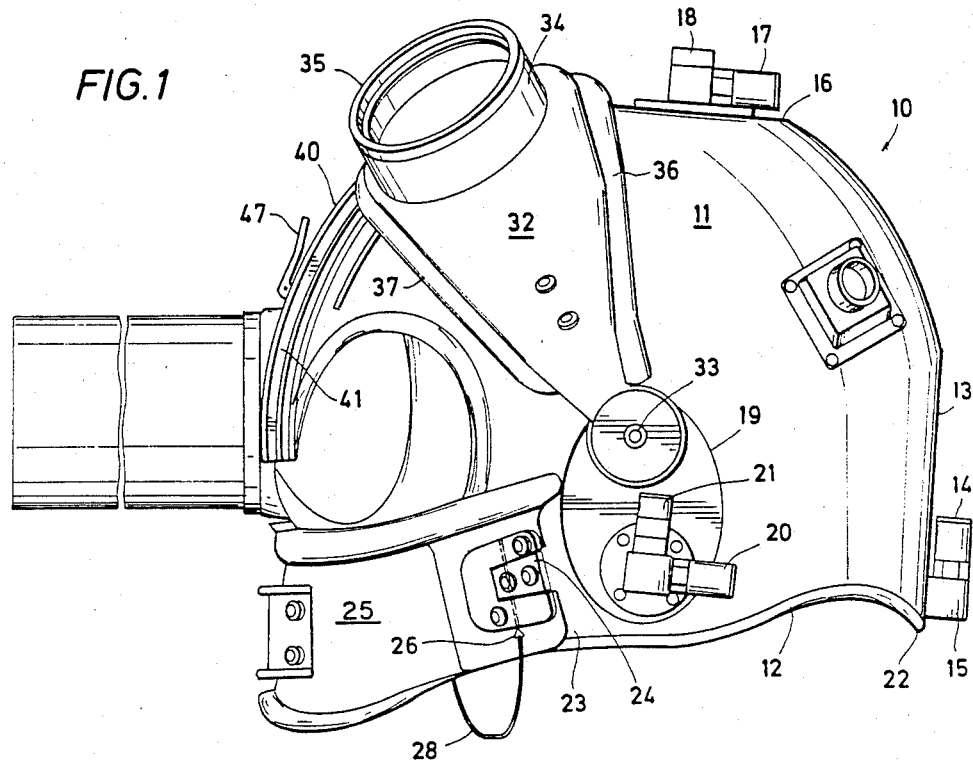
FIG. 1 is a side view of the improved helmet of the present disclosure showing the rotatable visors for covering the eyes with one visor raised and one visor down.

Attention is directed to FIG. 1 of the drawings where the numeral 10 identifies the helmet of the present disclosure. It is constructed with an outer shell 11 of solid plastic material, the ideal material being a lightweight elastomeric product, one acceptable material being polyethylene. The helmet interior is shaped to conform with the head and is sized dependent on the size of the head of the user. The shell is constructed with a padded border 12 which has the form of a bead which covers the shell edge. It is shaped generally in the fashion of a pilot's helmet with several modifications as will be noted. For instance, in FIG. 1 there is a flat spot 13 at the back to enable mounting of accelerometers 14 and 15 at right angles to one another. Likewise, there is an additional flat spot 16 on the top of the helmet for mounting of similar accelerometers 17 and 18 arranged at right angles to one another. Last of all, there is a flat spot 19 which again is provided for mounting of accelerometers 20 and 21 at right angles to one another. On the opposite side of the helmet but obscured, there is an additional flat spot similar to the region 19 for mounting another pair of orthogonal accelerometers or other sensors. The helmet is cut away so that the bottom or edge of the helmet at 22 is comparatively high with respect to motorcycle helmets and the like. The bottom edge extends forwardly to a region which is identified at 23 which, when on the head of a user, is located forward and slightly below the ear. This will be described as the cheek piece 23 for purposes of nomenclature. The cheek piece 23 protrudes forwardly and slightly downwardly to thereby position a two part clasp 24 at this area. The clasp 24 supports a chin bar 25 which extends forwardly, downwardly and in a curving fashion to encircle the lower chin of the user. The two part clasp includes a U-shaped sliding lock portion fitting on three sides against an upstanding, conforming clasp base anchored on the shell 11. The two are releasable locked together by a pin 26 inserted into aligned holes in the clasp portions. The pin is frictionally held in place but it is easily pulled out by a lanyard 28. The two ends of the lanyard connect to duplicate pins at duplicate clasps on both ends of the chin bar 25.

Figure 2:
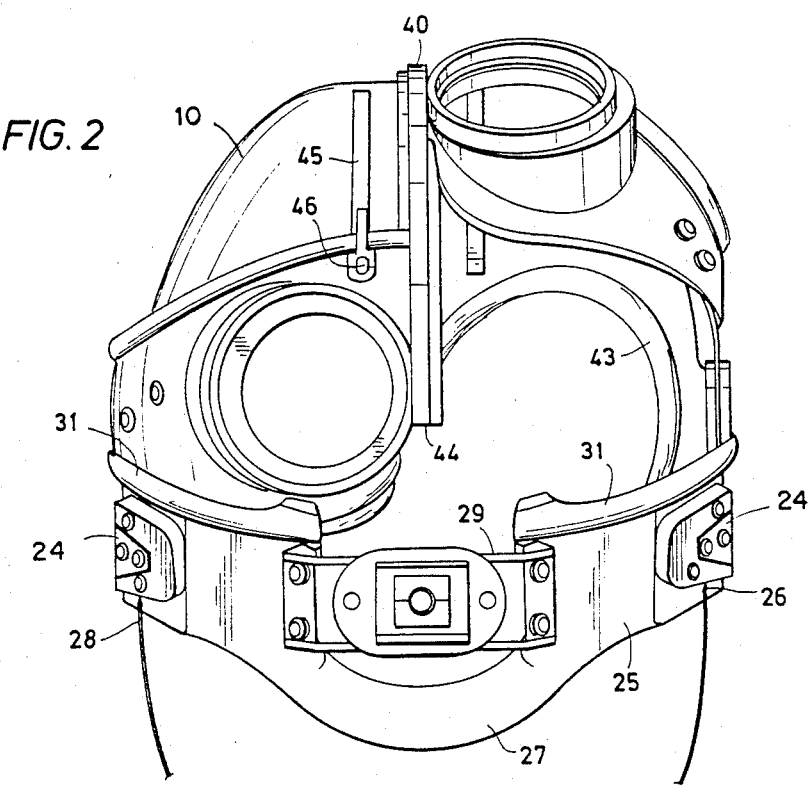
FIG. 2 is a view of the front of the helmet at right angles to the view of FIG. 1 again showing one of the visors raised and the other lowered.

The chin bar 25 is symmetrical with similar left and right portions on both sides as shown in FIG. 2 of the drawings. The central portion 27 dips below a cut away area which is immediately in front of the mouth of the user. The chin bar 25 supports a demountable bite bar 29 which spans the gap above the central chin bar portion 27. The bite bar 29 includes the rectangular frame with a central mounting mechanism to be discussed in regard to FIG. 3. Individualized bite bars are mounted releasably on the frame for quick conversion. The demountable system thus contemplates an individualized and shaped mouthpiece (to be described) which is supported on the bite bar and extends rearwardly so that it can be gripped comfortably in the fashion of a mouthpiece. This system enables more than one person to use the helmet 10 and yet each person can easily have a customized system for their head shape. An important feature is the quick disconnect system operated by pulling downwardly on the lanyard 28. In the event of nausea or motion sickness symptoms, the user can quickly pull downwardly on the lanyard, removing the clasp pins 26 and thereby unlatching the chin bar and supported mouthpiece. This quickly clears the mouth and reduces risk of choking the user with the mouthpiece.

It will be observed that the upper edge of the chin bar 25 is equipped with cloth and back material 31, this serving as a light seal which will cooperate with the lower edges of the respective visors to be described. In FIG. 1 of the drawings, a left eye visor 32 is shown in a pivoted position. It is supported at a rotatable pivot 33 which is affixed to the side of the helmet. The visor inscribes an angle appropriate to provide sufficient height for an eyepiece 34. The eyepiece 34 supports an encircling ring 35. The ring is a mount for a lens so that the user may look through the visor or alternatively through other equipment to be described. The mount ring 35 is constructed in the fashion of mounting rings on cameras, the preferred form permitting lenses or other optical devices to thread to the mounting ring for support on the visor. Examples of the devices will be given later. The diameter of the opening is sufficient that the user has an adequate field of vision through the opening.

The visor 32 is a wedge shaped curving plastic section. It is constructed to conform to the exterior curving shape of the helmet. It is built with an upper edge bead 36 which is thicker and again is made of softer material. A contoured edge 37 is located along the lower edge of the visor to mesh with the cloth and hook material 31 along the top of the chin bar 25. The bead 36 snugly contacts against the outer skin of the helmet shell 11 to limit light leakage which might otherwise pass under the visor. In this sense, the visor assists in forming a light leak barrier to avoid distraction of the user from lateral light entry into the helmet. The visor encircles or inscribes an angle of approximately 90° around the periphery of the helmet. Thus it is fastened at the pivot 33 at one end. It is larger at the opposite end and terminates at a tongue for engaging a tongue and groove guide or track 40. The track 40 is symmetrical along the center line of the helmet and is positioned immediately over the bridge of the nose and curves to the top of the helmet. It is an arc of a circle so that the visor may pivot around the pivot point 33 as shown in FIG. 1. The track 40 incorporates an undercut groove 41 as best shown in FIG. 1 and the groove cooperates with a protruding tongue along the edge of the visor. The tongue portion is received in the groove 41 to define a tongue and groove guide channel. Thus, one end of the visor is anchored for pivotal movement while the other end is guided in sliding movement in the track 40. This permits the visor to rotate through an arc of approximately 60° or 75° so that it has two positions. One position is shown in FIG. 2 where the left visor is located over the eye while the right visor has been rotated upwardly to a position out of sight of the wearer.

The visor construction shown in FIG. 2 enables the visor to rotate upwardly and discloses a larger eye socket on the shell 11. This is bordered with a light blocking bead 43 which covers over the edge of the shell 11. This extends forwardly to the lower end of the track 40. There, it tucks under the track where the track terminates at its lower extremity 44. This is located at the tip of the nose of the wearer when placed on their head.

In FIG. 2 of the drawings, a locking groove 45 is shown for one of the two visors. Both visors are provided with locking grooves. The locking groove curves along the shell 11 to define a narrow channel. The visor supports a pivotally mounted look pin 46 which is moved by a lever 47 (see FIG. 1). This pin passes through the visor and extends into the groove 45. When raised, easy movement of the visor is permitted. When the pin is extended, it inserts sufficiently into the groove 45 to engage internal groove surfaces to retard movement of the visor.

Figure 3:
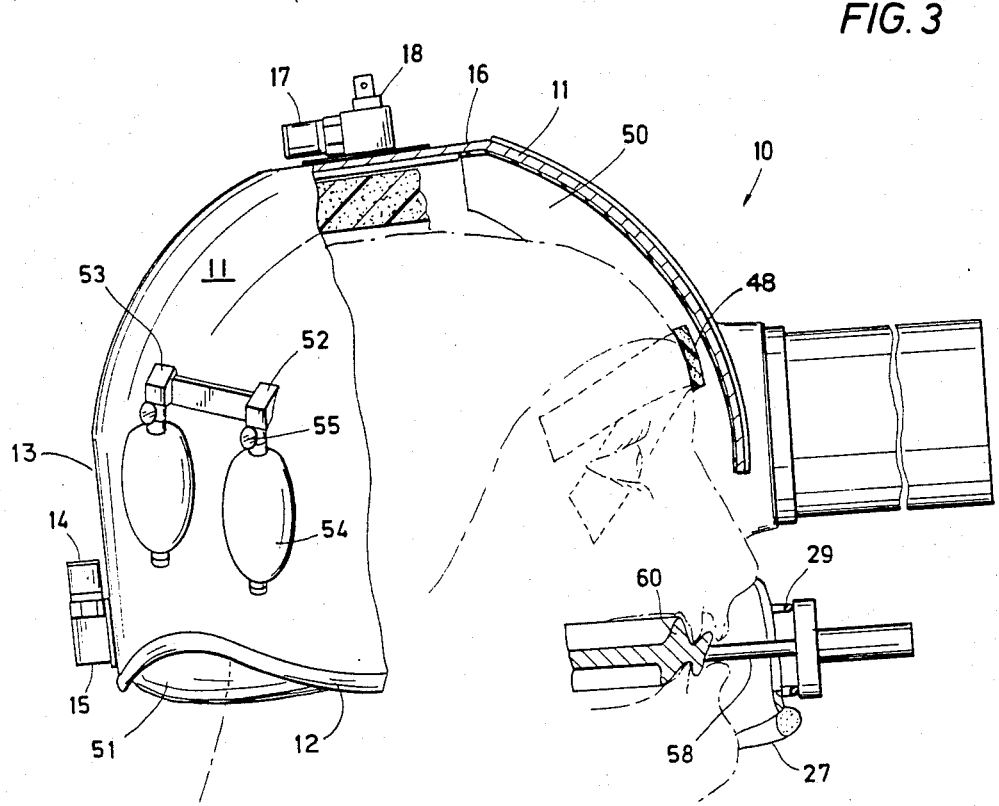
FIG. 3 is a view, partly in section through the helmet of FIG. 1, additionally showing a chin bar and individualized mouthpiece bearing against the teeth and hard palate to fix the helmet rigidly with respect to the skull.
Figure 4:
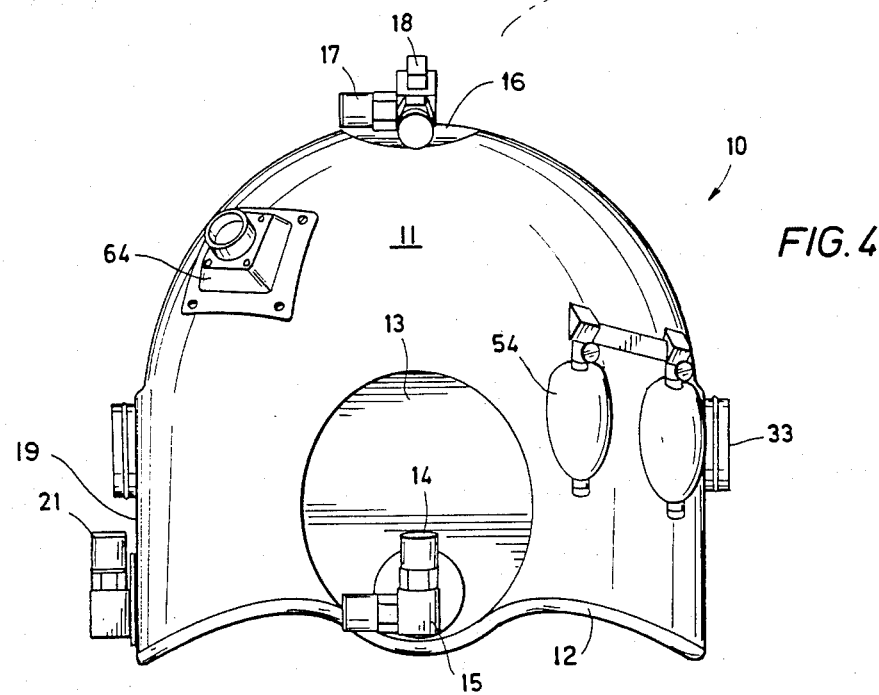
FIG. 4 is a view at right angles to the view of FIG. 3 further showing mounting systems for three pair of orthogonal accelerometers and also setting forth a bladder inflation system.

Attention is now directed to FIGS. 3 and 4 to be considered jointly. A reverse nape strap 48 loops forward of the forehead of the user to assist in firm helmet placement. A top bladder 50 is located inside the shell 11. The bladder contacts the crown of the head to the rear of the strap 48. It preferably is an inflatable bladder which supports a removable thin foam layer for contact against the top of the head of the user. The thin foam and bladder 50 are located in t he top central portion of the helmet. Another bladder 51 is included around the edge of the helmet and is constructed somewhat in the fashion of a horseshoe to encircle the back of the head at the neck and to extend along the side edges of the helmet near the ears. The bladder 51 supports a removable foam layer in the shape of a concentric horseshoe having suitable ear matching notches for headphones. This foam layer is removable to permit users with different size heads to wear the helmet. This serves as a forward anchor point to the helmet 10. The second bladder is generally U-shaped to provide lateral locking. It has been determined that additional bladders of relatively small volume can be used to fill out the remaining regions of contact against the head of the user. For instance, in one embodiment of the present apparatus, a total of four individual bladders beneath the shell and in contact (through foam layers) with the head of the user has been found acceptable. Each bladder is individually filled. To this end, they connect by suitable conduits (not shown) to externally located manifolds 52 and 53. The manifold 52 supports a squeeze bulb 54, and a bleed valve with an adjustable knob 55 is connected with the bulb 54. The bulb 54 is hand operated to pump air into one of the bladders and the knob 55 is closed to prevent drainage. In similar fashion, the manifold 53 supports an individualized squeeze bulb, again used in the same fashion. Ideally, an individual squeeze bulb is provided for each bladder so that they can be filled and yet not over filled. At the time of mounting the helmet, all of the various bladders are deflated; then, the bladders are filled and the helmet is then held snugly but comfortably against the head of the user. User's control of filling assures tailored comfort. It is extremely important to provide comfort because the helmet 10 of the present invention may be worn for many hours. Comfort is assured by the use of the inflatable bladders which yield, thereby conforming to the contours and shape of the skull.

An important feature is the incorporation of the bite bar support of the mouthpiece. It supports a small rod 58 which in turn supports an individualized mouthpiece 60. The mouthpiece grips the front and back surfaces of the upper front teeth and contacts the hard palate behind the front teeth. It is rigidly fixed by the bar 58 to the bite bar and hence to the helmet 10. This anchor point is very important to provide stability. This stability assures that the helmet is anchored without slippage and is otherwise immobilized on the head of the user. Because it is in contact with the hard palate, it can properly be described as anchored to the skull and hence relative motion between the helmet and the head of the user is impossible. Moreover this is achieved with a high level of comfort. That is the head is clamped and held but it is not brutalized by the incorporation of hard contacts against the head. The firmness of anchoring is accomplished with significant comfort to the user.

Figure 5:
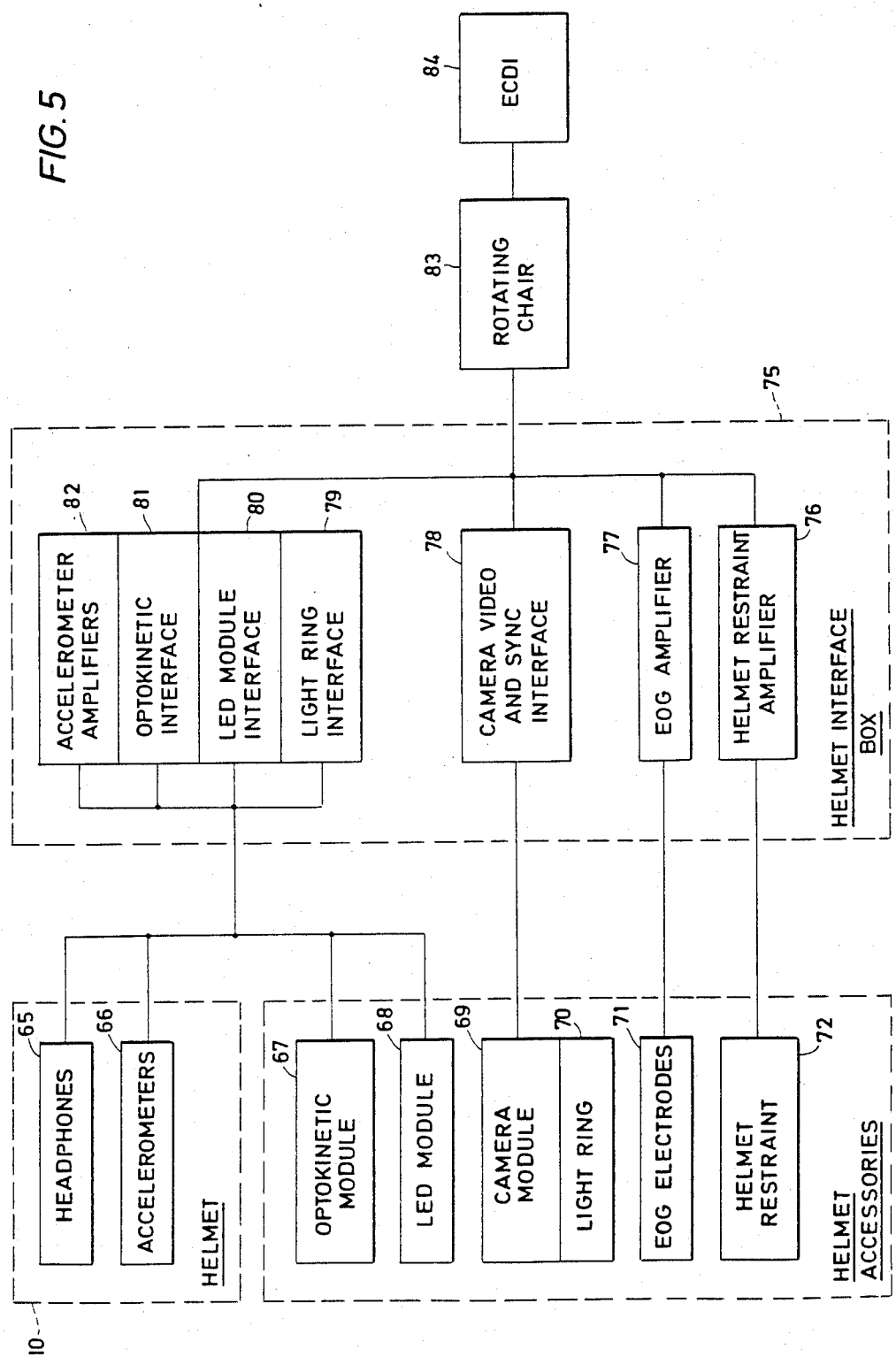
FIG. 5 is a schematic block diagram of the circuitry and other components which are helmet accessories and showing their connection with a helmet interface box for data signal processing.

Another important factor shown in FIG. 4 is the incorporation of an externally accessed electrical connector 64. This will be used for a number of sensors to provide electrical continuity to the exterior Going now to FIG. 5 of the drawings, this schematic block diagram shows the location of various components and accessories to be described Briefly, the helmet 10 supports headphones on the interior positioned over the ears, this being identified at 65. The several accelerometers are identified at 66. They are wired in the helmet on the interior of the shell and connect to the exterior through the electrical fitting 64. The head phones are used for communication with the subject. Additionally, and just as importantly, they are often used in experiments to transmit white noise and various tones to the subject to blank off audio stimuli This permits the experiments to proceed without audio interference. The helmet thus supports these components with wiring on the interior.

The numeral 67 identifies the optokinetic module. It is constructed in an optically opaque container and has a threaded connection which connects with the ring mount 35 shown in FIG. 1. Recall that both visors are equipped with duplicate ring mounts 35. They are threaded so that they receive demountable equipment in the fashion of placing a lens on a camera body. The optokinetic module is thus a closed housing which threads to one visor or the other and is positioned in the field of vision of one eye of the user. This field of view sees selected objects or graphics to cause the user to reposition their eye. This can be used to cause the subject to redirect their line of vision by a specified angle. The optokinetic module has an opaque housing which shuts out all other light and which provides the optical stimulus for the user. This type device is located on one visor or the other so that the viewer can see the image in their field of vision.

The LED module 6B is structurally similar to the module shown in FIG. 1. It has a closed and opaque housing which mounts in the same fashion as shown in FIG. 1 to the visor, and it is used to position a set of controllably activated LEDs across the field of view so that first one and then another can be illuminated. They are located so that the observer will deflect their vision from first one and then to another.

Another module is identified at 69. It includes a video camera in the module. In addition to that, it has an integrally constructed light ring 70. Again, the housing is shaped so that it is opaque, threadably mounted to the visor and within the field of vision of the user. The camera module is a small video camera which is aimed at the eye of the user. Since all light is shut out, the eye must be illuminated. The light ring 70 is included to provide adequate illumination for the camera. For comfort of the subject, one approach is to provide illumination with infrared lamps and to use a camera which responds to infrared light. Thus, the camera module is a small video camera with appropriate optics for focusing on the eye.

The camera module 69 cooperates with either module 67 or 68. Fortunately, when an optical stimulus is provided at one eye, the other eye responds also. Thus, if the subject sweeps their line of vision to the right, as prompted by one of the optical stimuli, the other eye will deflect in like fashion. Because this coupling between the two eyes persists the stimulus can be provided to one eye and the response of the subject can be observed in the other eye. For this reason, the two independent visors are included in the helmet 10. The camera can be mounted on one visor and the module providing the stimulus is then mounted on the other visor.

An important aspect of the testing of eye movements if the incorporation of electrodes which measure the electrooculography (EOG). EOG electrodes are included at 71. They are mounted on the face of the subject near the eye with ready access as shown in FIG. 3 of the drawings. The numeral 72 identifies various helmet restraints.

A helmet interface box is included at 75. It is mounted away from the helmet to reduce mass of the helmet. Conveniently, it can be placed on the back of the chair on which the subject sits. This includes an amplifier 76 which is provided with the signals from the helmet restraint circuitry 72. Likewise, another amplifier system 77 is included for the EOG electrodes. Recall that the camera module 69 includes a video camera. The appropriate video and synchronization signals are provided through an interface 78. The light ring 70 is connected with a suitable power source which is the light ring interface 79. The LED module 68 is likewise provided with a suitable interface 80. An appropriate interface for the optokinetic module 67 is also included at 81. The several accelerometers 66 are connected with appropriate amplifiers 82. All of this data is then provided by a wiring harness in a rotating chair 83 for convenience in conducting such experiments. In turn, that data is then delivered to an experiment control and data interface 84 which then connects the various data to a computer with an adequate memory system for data storage. Accordingly, the data can then be processed with a view of reducing space adaptation syndrome in motion sickness and thereby obtain an indication and hopefully a system for reducing motion sickness.

While the foregoing is directed to the preferred embodiment, the scope thereof is determined by the claims which follow.

We claim:

1. A neurosensory helmet comprising:
    (a) a rigid shell to surround the head of a test subject, said shell having large front facial cutouts resulting in a centrally extending nose portion;
    (b) means for coupling said shell relative to the skull of said test subject to prevent relative movement between said shell and the skull, without restraining head movement of the test subject;
    (c) means for sensing eye and head movement of the test subject; and
    (d) means for sealing out the entrance of extraneous light from the test subject.

2. The apparatus of claim 1 including a positive lock means joining said visor means to said track means.

3. The apparatus of claim 2 wherein said visor means is a pair of symmetrical left and right visor means, each thereof having a side located pivot means and each having a separate positive lock means connected to said track means for independent movement.

4. The apparatus of claim 1 including three dimensional responsive means for sensing movement of said shell in space and forming signals indicative thereof.

5. The apparatus of claim 4 wherein said responsive means comprises orthogonal accelerometer means.

6. The apparatus of claim 4 including shell mounted electrical connector means Connecting to:
    (a) said responsive means; and
    (b) headphones in said shell.

7. The neurosensory helmet of claim 1 in which:
    the coupling means comprises fillable air bladders between the inside of the shell and the skull of the test subject and a bite bar connected fixedly to a mouthpiece bearing against the teeth and the hard pallet of the test subject, the bite bar being connected to a forwardly and downwardly directed separable chin bar extending from one side of the shell to the other.

8. The apparatus of claim 7 including a U-shaped air filled bladder encircling the person at the back of the head and extending forwardly toward the ears of the person, hand operated means for filling said bladder, and also including separate alternate bladders wherein said bladders are between shell and the skull of the person.

9. The apparatus of claim 8 wherein valve means are connected to said bladders for releasing air therein.

10. The neurosensory helmet of claim 7 in which:
    releasable means connects said chin bar to said shell for instant release of the chin bar upon actuation by the test subject.

11. The neurosensory helmet of claim 7 in which the means for sensing eye movement are mounted on independent visor means pivotally mounted on the side of the shell and having an elevated position and a second position in front of the eyes of the test subject, said visor means being guided by a single track means extending along the centrally extending nose portion between said elevated position and said second position.

12. The apparatus of claim 11 wherein said visor means comprises:
    (a) left and right separate visor means;
    (b) separate pivot means for each of said left and right visor means;
    (c) separate holes for the left and right eyes of the person, said holes being formed in said separate visor means; and
    (d) mounting means adjacent said holes for mounting optical means relative to said holes for visual use by the person.

13. The apparatus of claim 12 wherein said mounting means comprises lens mounting means.

14. The apparatus of claim 13 including:
    (a) first means mounting on said mounting means for visually stimulating one eye of the person; and
    (b) second means mounting on said mounting means for optically observing the remaining eye of the person.

15. The apparatus of claim 14 wherein said first means comprises means forming a bright pot in the person's field of vision at selected locations.

16. The apparatus of claim 14 wherein said second means comprises a camera directed at the remaining eye of the person.

17. The apparatus of claim 16 including infrared lighting means illuminating the remaining eye of the person.

18. The neurosensory helmet of claim 11 in which the light sealing means includes the chin bar having sealing means occluding light from below the chin area of the test subject; the visor and the chin bar having sealing means whereby when the visor is in the second position external light is occluded, and the top edge of the visor having sealing mans engaging with the shell to occlude external light.

* * * * *